United States Patent [19]

Guzzi et al.

[11] Patent Number: 4,547,521

[45] Date of Patent: Oct. 15, 1985

[54] 16-METHOXY-16-METHYL PROSTAGLANDIN $E_1$ DERIVATIVES, A PROCESS FOR PREPARING THEM AND THEIR USE AS GASTROPROTECTIVE AGENTS

[75] Inventors: Umberto Guzzi, Milan; Romeo Ciabatti, Novate Milanese, both of Italy

[73] Assignee: Gruppo Lepetit S.p.A., Milan, Italy

[21] Appl. No.: 553,470

[22] Filed: Nov. 18, 1983

Related U.S. Application Data

[63] Continuation-in-part of Ser. No. 135,561, Mar. 31, 1980, abandoned.

[30] Foreign Application Priority Data

Apr. 10, 1979 [IT]  Italy ............................... 21707 A/79

[51] Int. Cl.$^4$ ................. C07C 177/00; A61K 31/557
[52] U.S. Cl. ................................... 514/530; 514/573;
560/121; 562/503
[58] Field of Search ....................... 560/121; 562/503; 424/305, 317

[56]  References Cited

FOREIGN PATENT DOCUMENTS 837865  7/1976  Belgium ............................... 560/121

*Primary Examiner*—Robert Gerstl
*Attorney, Agent, or Firm*—William J. Stein; Stephen L. Nesbitt; Gary D. Street

[57]  ABSTRACT

The present invention is directed to new 16-methoxy-16-methyl prostaglandin $E_1$ derivatives of the following general formula

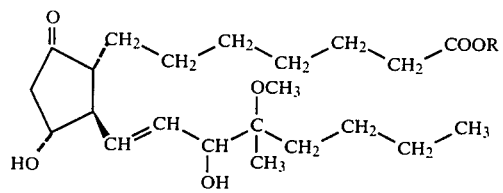

wherein R stands for a $(C_{1-4})$ alkyl group or a non-toxic pharmaceutically acceptable cation, to a process for preparing them and to their use as gastroprotective agents.

5 Claims, No Drawings

16-METHOXY-16-METHYL PROSTAGLANDIN $E_1$ DERIVATIVES, A PROCESS FOR PREPARING THEM AND THEIR USE AS GASTROPROTECTIVE AGENTS

This is a continuation-in-part of application Ser. No. 135,561 filed on Mar. 31, 1980, now abandoned, which application claims priority of Italian application Ser. No. 21707 filed on Apr. 10, 1979.

The present invention relates to new 16-methoxy-16-methyl prostaglandin $E_1$ derivatives, to a process for preparing them and to their use as gastroprotective agents, intending with the term "use" all industrially applicable aspects and acts of said use, including the embodying of the novel compounds into pharmaceutical compositions which therefore represent a further specific aspect of the present invention.

The novel compounds which form the first object of the present invention are optically active 16-methoxy-16-methyl prostaglandin $E_1$ derivatives of the following general formula

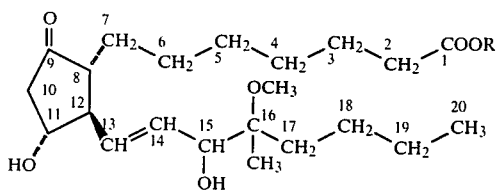

wherein R stands for a $(C_{1-4})$alkyl group or a non-toxic pharmaceutically acceptable cation, such as $Na^+$, $K^+$, the ammonium cation and its organic derivatives.

In the above formula, dotted lines are used to indicate that a particular substituent lies below the plane of the molecule as drawn ($\alpha$ configuration) while a heavy solid line is employed for a substituent which lies above the plane of the molecule as drawn ($\beta$ configuration).

The prostaglandin-like compounds of the above formula possess two chiral centers on the lower side chain i.e. at C-15 and C-16. Therefore four different isomers of formula I may be prepared characterized by the following combinations of configurational assignments at C-15 and C-16: (15-R, 16-S), (15-S, 16-R), (15-R, 16-R) and (15-S, 16-S). A preferred group of compounds of the invention are those of formula I characterized by a chirality at $C_{16}$ corresponding to that at $C_3$ of the stereoisomers of 3-methoxy-3-methyl-2-oxo-heptyl-phosphonic acid dimethyl ester which has an $[\alpha]_D^{20} = +41.2°$ (c=1% in $CHCl_3$) and having a chirality at $C_{15}$ corresponding to that of the more polar stereoisomers of 9-acetoxy-15-hydroxy-16-methoxy-16-methyl-11$\alpha$-[(tetrahydro-1H-pyran-2-yl)oxy]prosta-13(E)-ene-1-oic acid methyl ester, which is the second eluted product in a chromatographic separation of stereoisomers on silica gel using a sequentially a mixture of petroleum ether/ethyl ether 8:2 (v/v) and petroleum ether/ethyl ether 6:4, (v/v), as the eluent. Therefore the absolute configuration of the compounds of the invention at the $C_{15}$ and $C_{16}$ is one of the following combinations: (15R, 16R), (15S, 16R), (15R, 16S), and (15S, 16S).

A preferred compound is the stereoisomer of the 11$\alpha$-15-dihydroxy-16-methoxy-16-methyl-9-oxo-prosta-13-(E)-ene-1-oic acid methyl ester having a chirality at $C_{16}$ corresponding to that at $C_3$ of the stereoisomer of 3-methoxy-3-methyl-2-oxo-heptyl-phosphonic acid di- methyl ester which as an $[\alpha]_D^{20}$ of $+41.2°$ (c=1%, $CHCl_3$) and having a chirality at $C_{15}$ corresponding to that of the more polar stereoisomers of 9-acetoxy-15-hydroxy-16-methoxy-16-methyl-11$\alpha$-[(tetrahydro-1H-pyran-2-yl)oxy]prosta-13-(E)-ene-1-oic acid methyl ester, which is the second eluted product a chromatographic separation of stereoisomers on silica gel using sequentially a mixture of petroleum ether/ethyl ether 8:2 (v/v) and then petroleum ether/ethyl ether 6:4 (v/v).

The compounds which are the object of the present invention are endowed with a remarkable anti-secretory activity, particularly when they are administered by the oral route, and show, even at very low oral doses, outstanding cytoprotective effects.

Prostaglandins make up a class of natural substances which are being investigated in depth because they possess different pharmacological actions (abortifacient, antisecretory, hypotensive, bronchodilator) and also because they are involved in many biological processes (W. Losert et al., Arzneim. Forsch. Drug Res., 25, No. 2, page 135, 1975). Therefore vast literature exists in this field and there are also a number of patents and patent applications claiming classes of "synthetic" prostaglandins which differ from the naturally occuring ones in the structure of the cyclopentane ring and/or one or both of the side chains (see for instance U.K. Pat. Nos. 1.409.841, 1.506.816, and 1.345.934, Belgian Pat. No. 827.529 and U.S. Pat. No. 4.029.698). The same prostaglandins of formula I above which are the object of the present invention, even though completely novel per se, are encompassed by the general formulae of Belgian Pat. No. 837.865 and of U.K. Pat. No. 1.495.152. However, in the above Belgian Patent, 16-methyl-16-methoxy-prostaglandin $E_1$ derivatives having a saturated bond at C-5 are never described, while in U.K. Pat. No. 1.495.152 only two 16,16-dimethyl prostaglandins E are prepared wherein, moreover, the methylene group at position 17 is replaced with an oxygen atom which, in its turn, bears a propyl or pentyl group, and a cis-5-double bond is always present.

The compounds of the present invention are prepared according to known methods which are commonly employed in this field and are exhaustively described in Belgian Pat. No. 837.865. The starting compound is a cyclopentane aldehyde of the formula

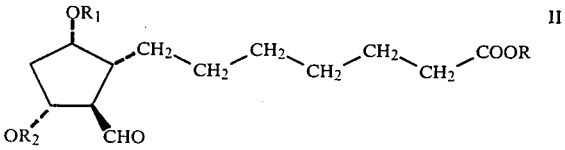

wherein R is as described above and $R_1$ and $R_2$, each independently, represent hydrogen or a protecting group of the hydroxy function. Preferably for the scope of the present invention, $R_1$ represents a $(C_{2-4})$aliphatic acyl and $R_2$ is hydrogen or a tetrahydro-1H-pyran-2-yl radical.

The starting cyclopentane aldehyde may be prepared through methods described in the literature (see for instance Belgian Pat. Nos. 807.161 and 837.865).

The process for preparing the prostaglandin-like compounds of the present invention comprises as the first step the condensation between the aldehyde of formula II above and a phosphonate reagent of the following general formula

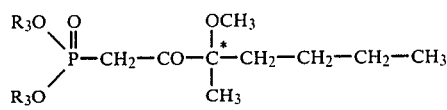

wherein $R_3$ is an alkyl group of from 1 to 4 carbon atoms, to yield an intermediate compound of the formula

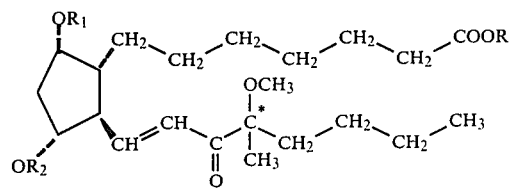

wherein R is as defined above, $R_1$ and $R_2$, each independently are hydrogen or protecting groups of the hydroxy functions and preferably $R_1$ is a $(C_{2-4})$aliphatic acyl and $R_2$ is hydrogen or the tetrahydro-1H-pyran-2-yl radical.

The condensation is carried out substantially under the same conditions which are described in the chemical literature concerning synthesis of prostaglandins from cyclopentane aldehyde precursors and phosphorous reagents. In practice it is carried out in the presence of an inert organic solvent such as for instance tetrahydrofuran, dimethoxyethane, benzene, dioxane, and the like, at a temperature comprised between 0° and 80° C.

For carrying out the condensation, the phosphonate reaction partner has to be transformed into the corresponding anion and for this purpose about one equimolecular proportion (calculated on the phosphonate of formula III) of an alkali metal hydride is employed. As above stated, the phosphonate of formula III possesses a chiral center at $C_3$ (which is indicated in the above formula III by an asterisk) and it is preferably used in an optically active form. However it can be used also as a mixture of the two possible isomers. The condensation between the aldehyde of formula II and a mixture of the two isomers of the phosphonate of formula III therefore affords a mixture of the two possible isomers of formula IV having the opposite absolute configuration (one R and the other S) at C-16, while the use of an optically active form of the phosphonate III yields a compound of formula IV having a given configuration at C-16 (R or S). If a mixture of the two possible isomers at C-16 is obtained, it may be separated into the two isomeric forms by means of known techniques, as an example, by chromatographic methods. In any case, even if not absolutely necessary, it is advisable to separate the single isomers before further processing the intermediates IV. Thus the second step of the reaction pathway comprises reduction of the 15-keto compound to the corresponding 15-hydroxy derivative by means of commonly employed reducing agents, such as sodium borohydride, zinc borohydride, diphenyl tinhydride or lithium trialkyl borohydrides.

Considering that the reduction of the oxo group at C-15 causes the introduction of a further chiral center, and that, as indicated above, the reduction is more advantageously carried out separately on the two possible isomers of formula IV, from each of the C-16 isomers a mixture of two products of formula V is obtained having the same configuration at C-16 (R or S) and opposite configuration (R and S) at C-15

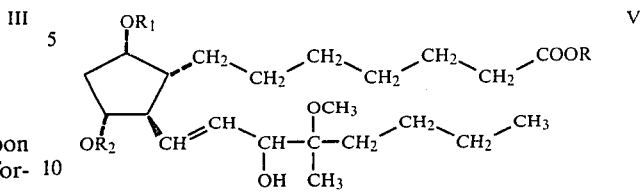

The mixture of the two isomers of formula V thus obtained may be employed as such in the subsequent reaction steps but they are preferably separated into the two single isomers which will then undergo, separately, the same reactions. Thus, in the former case a mixture of end products of formula I is obtained which, if desired, may be separated into its components while in the latter case, the use of a single isomer with given absolute configurations at C-15 and C-16, leads to only one of the possible isomers of formula I.

It has been noted that when the reduction is carried out on a compound of formula IV wherein $R_2$ is hydrogen and, preferably, the carbon atom at position 16 has one of the two possible absolute configurations, the two C-15 isomers are obtained in quite different amounts.

Sometimes one of the C-15 isomers, and generally the most polar one, is obtained in very small amounts. Surprisingly it has been found that if the reduction is carried out on a compound of formula IV wherein $R_2$ is a protecting group for the hydroxy function, preferably, the tetrahydro-1H-pyran-2-yl radical, the two isomers are obtained in approximately the same ratio. In this case, the subsequent separation according to known methods such as, for instance, silicagel column chromatography or preparative thin layer chromatography using silica gel plates, yields the two single products of formula V wherein the hydroxy group at position 11 is protected, preferably, as a tetrahydro-1H-pyran-2-yl ether. However, depending on the configuration at C-16, it may be necessary, or convenient, before submitting the mixture to chromatographic separation, to restore the free hydroxy function at position 11.

According to a preferred embodiment of this invention, a molar proportion of the compound of formula IV wherein $R_1$ represents a protecting group of the hydroxy function, preferably, a $(C_{2-4})$aliphatic acyl, and $R_2$ is hydrogen, having a given absolute configuration at C-16, is reacted with about 2–3 equimolecular proportions of 2,3-dihydrofuran in the presence of an anhydrous inert organic solvent, such as benzene, and a catalytical amount of p-toluenesulfonic acid. The reaction is conducted at room temperature and takes from about 5 to about 20 minutes. A compound of formula IV is thus obtained wherein R is as defined above, $R_1$ is a protecting group for the hydroxy function, preferably a $(C_{2-4})$aliphatic acyl group, and $R_2$ is the tetrahydro-1H-pyran-2-yl radical.

The subsequent reduction of the oxo group at C-15 gives the corresponding compound of formula V (as a mixture of the two possible isomers at C-15) wherein $R_2$ is the tetrahydro-1H-pyran-2-yl radical. Generally it is desirable to separate the mixture thus obtained into the single C-15 isomer according to the procedures described above. The mixture, or the single isomers, are then further processed to yield the end products of formula I. The reaction steps which, starting from a compound of formula V, lead to a final compound I, comprise protecting the hydroxy groups at positions 11 and 15 of the compounds of the above formula V by reacting with an appropriate protecting agent, preferably 3,4-dihydro-2H-pyran, hydrolysing the obtained 11,15-protected compound of formula V under mild conditions, for instance with sodium or potassium carbonate when $R_1$ is a $(C_{2-4})$aliphatic acyl group, restoring the free hydroxy group at position 9, oxidizing said hydroxy group to an oxo group utilizing common oxidation procedures (for instance with the Collins reagent i.e. the complex pyridine/chromium oxide) and finally removing the protecting groups at positions 11 and 15.

When the protecting groups of the hydroxy functions at positions 11 and 15 are tetrahydro-1H-pyran-2-yl radicals, their removal is preferably carried out through acid hydrolysis with a mixture acetic acid:water:tetrahydrofuran=19:11:3 (v/v/v) at a temperature of 40°–45° C.

If these reactions are carried out on a mixture of compounds of formula V having the same absolute configuration at C-16 and opposite configurations at C-15, a mixture of two isomers at C-15 of formula I is obtained. Said mixture is preferably separated into the single isomers by means of the usual chromatographic techniques illustrated above.

The starting phosphorous reagents of formula III are prepared by condensing a methylphosphonic acid lower alkyl ester of formula VI

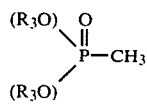

VI wherein $R_3$ represents a $(C_{1-4})$alkyl group, with an α-methyl-α-methoxy-hexanoic acid lower alkyl ester (or the corresponding acyl chloride) of formula VII

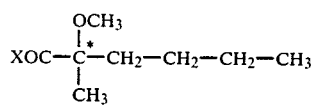

VII wherein X may represent —$OR_3$ or —Cl.

This procedure involves transforming the methylphosphonate of formula VI into the corresponding anion by the addition of butyl lithium at −78° C. in tetrahydrofuran and then contacting it with the compound of formula VII for about 1 hour at the same temperature. When an optically active form of the phosphonate of formula III is desired, the racemate of the α-methyl-α-methoxy-hexanoic acid is resolved into the two antipodes by conventional procedures, such as using an optically active base like ephedrine, atropine or amphetamine, to form the corresponding salts which are then separated by fractional crystallization.

The separated antipodes are then transformed into the corresponding optically active esters or acid chlorides of formula VII which in their turn are condensed with the methylphosphonate of formula VI.

By analogous structure correlation studies with substances of known absolute configuration, the optically active phosphonate reagent of formula:

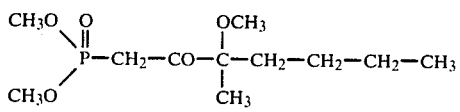

having an optical rotation of +41.2°, i.e., $[\alpha]_D^{20} = +41.2°$ (c=1% in $CHCl_3$), was assigned the "R" absolute configuration. Therefore its chemical name is 3R-3-methoxy-3-methyl-2-oxo-heptylphosphonic acid dimethyl ester. Since the reaction steps of the process for preparing the compounds of the invention does not modify the chirality of the above reactant, the "R" absolute configuration is retained in the corresponding $C_{16}$ of the compounds of formula I.

The compounds of the present invention are also potent inhibitors of the gastric secretion when they are administered to laboratory animals by the oral route. The extent of this biological activity could not be foreseen by a person skilled in this field, considering that the corresponding compounds with a 5-double bond, which are described in Belgian Pat. No. 837.865, when administered per os are far less active. In other words it has been found that a slight modification in the structure of these compounds has generated remarkable and favourable changes in the biological activity. The gastric antisecretory properties of these compounds when administered per os were evaluated on the basis of their effectiveness in inhibiting the hyperacidity induced by histamine in dogs. Histamine, which is a potent stimulator of the acidic gastric secretion (see Bertaccini et al., Eur. Journ. Pharmacol., 28, 360, 1974), was administered intravenously by continuous infusion during the experiments.

A group of five mongrel dogs was used in the experiment. The dogs were surgically treated according to the method described by Bertaccini et al., (see above) in order to provide each animal with an innervated main stomach or gastric fistula (G.F.) and a denervated stomach or Haidenhain pouch (H.P.). The main stomach and the Haidenhain pouch were each equipped with a cannula in order to allow the gastric juices to drain to the exterior by gravity.

Said gastric juices were then separately titrated with 0.1N NaOH by means of an automatic titrator (Radiometer, Copenhagen). The five dogs, after a period of four to five weeks of recovery, were first treated with the secreting agent alone (doses of histamine were increased progressively every 30 minutes from a minimum of 40 to a maximum of 320 µg/kg/h) in order to stimulate the acidic gastric secretion both in the G.F. and in the H.P.

Every thirty minutes the acidic output both from the G.F. and the H.P. was collected and titrated as described above. The values thus obtained (each one as a mean of five dogs) were considered as the "control values" or "controls".

To evaluate the gastric antisecretory oral activity of the compounds of the invention, they were administered by gavage into the main stomach at a given dosage, expressed as µg/kg/h, dissolved in 1 ml of physiological solution, 60 minutes before the secreting agent. The agent stimulating the gastric hypersecretion was administered intravenously by continuous infusion at the dosages indicated before, and every thirty minutes the gastric juices from both the G.F. and the H.P. were collected and titrated. In so doing it was possible to establish by simple calculations the percentage inhibition of acidic gastric secretion at given dosages of histamine and active compound.

The results obtained with the compound of example 1F show that very low dosages, from 25 to 100 μg/kg/h inhibit the gastric hyperacidity induced by doses varying from 40 to 160 μg/kg/h of histamine, of from about 95 to about 35% (calculated versus the controls) in the G.F. and from about 60 to about 30% in the H.P.

Under the same experimental conditions, the corresponding compounds bearing a C-5 double bond are almost inactive. Another experiment carried out under the same conditions as above but administering histamine at a fixed dose of 160 μg/kg/h instead of at increasing doses, showed that the compound of example 1F blocks the gastric acid secretion of about 60% while the corresponding compounds with a double bond at C-5 are inactive. The compounds of the present invention are potent inhibitors of also gastric hypersecretion also when administered intravenously. This has been confirmed by evaluating the effects, on gastric hypersecretion induced by histamine, produced by a single intravenous administration to anesthetized rats of the compounds of the present invention. The experiments were carried out essentially according to the methodology described by Ghosh and Schild in Brit. J. Pharm. (1958), 13, 54–61. According to this technique the rat is anesthetized with urethane and its stomach is perfused with a dilute sodium hydroxide solution (N/4000 NaOH at a rate of about 1 ml/min) by way of the oesophagus. The pH of the fluid emerging from a cannula in the pylorus is continuously recorded by means of a glass-electrode connected to a direct reading pH-meter and thence to a recorder. In passing through the stomach, the perfusate collects sufficient buffer to act as an approximately linear buffer system over the relevant range, so that the change in pH becomes a measure of acid secretion.

When the N/4000 NaOH solution is collected after having passed through the unstimulated stomach it gives an initial value of about 6–6.5 ($pH_{unstimulated\ stomach}$). A secretory stimulant, histamine in the present case, is then administered intravenously by continuous infusion at a dose of 1.5 mg/kg/h. After a few minutes the pH begins to fall and after about 10 to 20 minutes the secretory effect reaches its maximum and the pH its lowest value ($pH_{histamine\ stimulated\ stomach}$) which, owing to the continuous infusion of histamine, remains constant. The compounds to be tested are then administered intravenously and the pH is continuously recorded. By considering the highest pH value recorded, which evidences the maximum antisecretory effect reached with the test compound ($pH_{M.A.E.}$) and using the following equation $$\frac{pH_{M.A.E.} - pH_{H.S.S.}}{pH_{U.S.} - pH_{H.S.S.}} \times 100$$

the percent inhibition of gastric acid secretion may be easily calculated. A 100% effect means that the compound tested, at the dose tested, returned the pH of the histamine stimulated stomach to the initial value of the unstimulated stomach, while a 0% effect means that the administration did not affect the gastric secretion induced by histamine.

In representative experiments with the compound of example 1F we obtained the following results:

| Dose (μg/kg) | % Inhibition of the acid gastric secretion |
| --- | --- |
| 2.5 | 15 |
| 10 | 63 |
| 20 | 90 |
| 50 | 100 |

Other experiments were carried out which showed that the compounds of the present invention also possess a remarkable cytoprotective activity which appears at very low oral doses. More particularly, the cytoprotective activity of the compounds of the present invention was evaluated on the basis of their effectiveness in inhibiting the formation and reducing the severity of gastric ulcers in rats caused by the administration of a high dose of 1-(p-chlorobenzoyl)-5-methoxy-2-methyl-3-indolyl-acetic acid (indomethacin). The cytoprotective activity occurred at oral doses which are by far lower than those which cause inhibition of the gastric acid secretion. In these experiments the rats were deprived of food the day before the beginning of the experiments but water was given ad libitum. The compounds to be tested were administered by the oral route as a suspension in 0.5% aqueous methocel solution (5 animals/dose), while indomethacin was administered intraperitoneally at 10,000 mg/kg in the same vehicle. Another group of rats (controls) was administered only with the ulcerogenic agent. The cytoprotective properties of the compounds of this invention were then expressed as "percent inhibition of the ulcers with respect to controls", which can be easily calculated by the following ratio:

$$\frac{A.U.D._{(controls)} - A.U.D._{(treated\ animals)}}{A.U.D._{(controls)}} \times 100$$

wherein $A.U.D._{(controls)}$ is the average ulceration degree of the stomachs of the controls and $A.U.D._{(treated\ animals)}$ is the average ulceration degree of the stomachs of the animals which received both indomethacin and the compound to be tested.

The A.U.D.s are calculated according to the method described by Thuillier et al. Chim. Ther., 3, 53, 1968, by examining the stomachs of the laboratory animals for possible ulcerations and assigning a score from 0 to 4 which depends on the number and the severity of the observed ulcerations: 0 indicates absence of any ulceration on the gastric wall; 4 indicates perforating ulcerations. A single ulceration degree (S.U.D.) is then calculated for each single stomach. The sum of the S.U.D.s divided by the number of the animals affords the A.U.D. of the stomachs of each group of animals.

In these experiments the compound of example 1F proved to be very active even at very low doses. In fact at a dose of 3 μg/kg (the lowest dose tested in these experiments) the percent inhibition of the ulcers with respect to controls was of about 43, while the $ED_{50}$ (i.e. the dose which provokes an inhibition of the ulcers with respect to controls of 50%), as calculated by extrapolation, was 6 μg/kg.

It is therefore clear that the major protective action on the gastric mucosa exerted by these compounds is by one or more mechanisms that are independent of inhibition of acid secretion. As is apparent from the results of this last experiment, this compound protects in doses which are far too small to significantly inhibit acid secretion.

From the above results it follows that the prostaglandin derivatives of the present invention are useful in mammals to reduce and control excessive gastric acid secretion and also to exert, even at very low doses, a protective action on the gastric mucosa thereby reducing and avoiding gastrointestinal ulcer formation. Thus, according to a further feature of the present invention, there are provided pharmaceutical or veterinary compositions comprising a prostaglandin-like derivative of formula I as the active ingredient.

In the exploitation of the invention the preferred administrative route of the new compounds is per os in the form of capsules, coated tablets or syrups. If desired, parenterally administratable dosage forms can also be prepared as injectable ampoules. These pharmaceutical dosages are formulated as known in the art (see for instance Remington's Pharmaceutical Sciences, 13$^{th}$ Ed., Mack Publishing Co., Easton, Pa.) and are prepared by common procedures. These dosage units may contain from about 5 to about 100 μg and preferably from about 10 to about 60 μg of active ingredient. In addition to the active ingredient, capsules and coated tablets may contain the usual pharmaceutically acceptable excipients such as inert diluents, lubricating and disintegrating agents. Syrups may contain conventional suspending, wetting, buffering, flavoring agents and preservatives. The dosage regimen for the prostaglandin-like compounds of the present invention in accordance with a gastroprotective treatment will depend upon a variety of factors including the type, age, and weight of the mammal. Good results can be obtained however by administering the prostaglandin compounds of the present invention, at a daily dosage range comprising between about 10 and about 300 μg, preferably in divided doses. It is however clear that a daily dosage beyond the above indicated range may also be employed depending on the individual conditions of the subject to be treated.

This invention is further illustrated by the following examples:

EXAMPLE 1

11α,15-dihydroxy-16-methoxy-16-methyl-9-oxo-prosta-13(E)-ene-1-oic acid methyl ester (15-R, 16-R) and (15-S, 16-R) or (15-R, 16-S) and (15-S, 16-S)

(A) To a mixture of 770 mg of an 81.8% suspension of sodium hydride in mineral oil (0.026 mole) and 30 ml of anhydrous dimethoxyethane, a solution of 8 g (0.030 mole) of optically active 3-methoxy-3-methyl-2-oxo-heptylphosphonic acid dimethyl ester having $[\alpha]_D^{20} = +41.2°$ (C=1% in CHCl$_3$) in 40 ml of dimethoxyethane is added dropwise. The resulting mixture is allowed to stand at room temperature for 15 minutes, then a solution of 4.08 g (0.013 mole) of 7-(5α-acetoxy-2β-formyl-3α-hydroxy-cyclopent-1α-yl)heptanoic acid methyl ester in 50 ml of anhydrous dimethoxyethane is gradually added thereto.

After standing at room temperature for 6 hours, the reaction mixture is then poured into an aqueous solution saturated with NaH$_2$PO$_4$ which is subsequently extracted with ethyl ether. The organic extract is dried over MgSO$_4$ and concentrated to dryness. The obtained residue is purified by silica gel column chromatography by eluting with ethyl ether:petroleum ether 1:1 (v/v).

Yield: 3.9 g of 9α-acetoxy-11α-hydroxy-16-methoxy-16-methyl-15-oxo-prosta-13(E)-ene-1-oic acid methyl ester wherein C-16 has absolute configuration R or S. $[\alpha]_D^{20} = +53.8°$ (C=0.81% in CHCl$_3$). NMR absoption peaks in CDCl$_3$ (δ): 0.89; 1.1–2.1; 1.29; 2.08; 2.30; 2.4–2.6; 3.21, 3.68; 4.11; 5.23; 6.87.

(B) A mixture consisting of 5 g (0.0113 mole) of 9α-acetoxy-11α-hydroxy-16-methoxy-16-methyl-15-oxo-prosta-13(E)-ene-1-oic acid methyl ester (prepared as described under paragraph (A)) dissolved in 150 ml of anhydrous benzene, 2.6 ml (0.0285 mole) of 2,3-dihydropyran and 70 mg of p-toluenesulfonic acid in 50 ml of anhydrous benzene is prepared at a temperature comprising between 5° and 10° C. and is then maintained at room temperature for about 10 minutes. The reaction mixture is washed first with an aqueous solution saturated with sodium bicarbonate and then with water. Evaporation of the solvent affords a residue which is purified by means of silica gel column chromatography, by eluting with petroleum ether: ethyl ether 7:3 (v/v). Yield 5 g of 9α-acetoxy-16-methoxy-16-methyl-15-oxo-11α-[(tetrahydro-1H-pyran-2-yl)oxy]-prosta-13-(E)-ene-1-oic acid methyl ester wherein the carbon atom at position 16 has absolute configuration R or S NMR absorption peaks in CDCl$_3$ (δ): 0.88; 1.1–3.0; 1.25; 2.06; 3.23; 3.3–4.8; 3.72; 5.20; 6.8–7.1.

(C) To a solution of 13.5 g of sodium borohydride in 400 ml of methanol, cooled to −20° C., a solution of 5 g (0.0093 mole) of 9α-acetoxy-16-methoxy-16-methyl-15-oxo-11α-[(tetrahydro-1H-pyran-2-yl)oxy]-prosta-13(E)-ene-1-oic acid methyl ester (prepared as illustrated under paragraph (B)) is added dropwise.

The resulting solution is kept at −20° C. for about 2 hours, then it is poured into an aqueous solution saturated with NaH$_2$PO$_4$ which is subsequently extracted with ethyl ether. The organic extract is dried over Na$_2$SO$_4$ and evaporated to dryness yielding a residue which is a mixture of the two possible isomers at C-15 of the 9α-acetoxy-15-hydroxy-16-methoxy-16-methyl-11α-[(tetrahydro-1H-pyran-2-yl)-oxy]-prosta-13(E)-ene-1-oic acid methyl ester. Said isomers are separated by eluting first with petroleum ether: ethyl ether 8:2 (v/v) to purify the crude mixture, and then with petroleum ether: ethyl ether 6:4 (v/v).

The first eluted product (2.05 g of pure product, less polar isomer) has the following NMR spectrum: main absorption peaks in CDCl$_3$ occurring at the following frequencies expressed in δ units: 0.90; 1.13; 1.1–2.9; 2.07; 3.28; 2.5–4.3; 3.73; 4.67; 5.20; 5.7–5.9.

The second eluted product (2.1 g of pure product, more polar isomer) has the following NMR spectrum in CDCl$_3$ (δ units): 0.93; 1.07; 1.1–2.9; 2.07; 3.28; 3.2–4.2; 3.72; 4.67; 5.20; 5.7–5.9.

The two products thus obtained have the same absolute configuration at C-16 (R or S) and opposite configurations at C-15. They therefore represent the couple of isomers having the following absolute configurations at C-15 and C-16:(15-R, 16-R) and (15-S, 16-R) or (15-R, 16-S) and (15-S, 16-S).

The subsequent chemical modifications which lead to the end products of formula I do not alter the stereochemistry at C-15 and C-16.

(D) 2.1 g of the more polar isomer of 9α-acetoxy-15-hydroxy-16-methoxy-16-methyl-11α-[(tetrahydro- 1H-pyran-2-yl)-oxy]-prosta-13(E)-ene-1-oic acid methyl ester, prepared as described under paragraph (C), are dissolved in 150 ml of anhydrous benzene. After cooling, 1.3 ml (0.0142 mole) of 2,3-dihydropyran and a solution of 75 mg of p-toluenesulfonic acid in 40 ml of anhydrous benzene are added and after 15 minutes the solution is poured into aqueous sodium bicarbonate. The organic layer is separated, dried over $Na_2SO_4$, and taken to dryness. The residue is purified by silica gel column chromatography by eluting with petroleum ether:ethyl ether=7.3 (v/v) to yield 2,1 g of 9α-acetoxy-16-methoxy-16-methyl-11α-,15-bis-[(tetrahydro-1H-pyran-2-yl)oxy]-prosta-13(E)-ene-1-oic acid methyl ester wherein the combination of the absolute configurations at C-15 and C-16 is one of the four possible ones.

NMR spectrum ($CDCl_3$): 0.92; 1.12; 1.15; 1.1–3.0; 2.07; 3.25; 3.32; 3.2–4.2; 3.70; 4.5–5.2; 5.3–5.6 (δ units). The compound thus obtained is dissolved in 200 ml of anhydrous methanol and 2.1 g of anhydrous potassium carbonate are added to the resulting solution.

After stirring at room temperature for 24 hours the mixture is poured into an aqueous solution saturated with $NaH_2PO_4$ which is subsequently extracted with ethyl ether. The organic phase is separated, dried over $Na_2SO_4$ and concentrated to dryness. 1.95 g of 9α-hydroxy-16-methoxy-16-methyl-11α-15-bis[(tetrahydro-1H-pyran-2-yl)oxy]-prosta-13(E)-ene-1-oic acid methyl ester (pure product) are obtained.

NMR spectrum in $CDCl_3$ (δ): 0.92; 1.0–2.9; 1.10; 1.13; 3.25; 3.32; 3.2–4.4; 4.6–5.0; 5.4–5.9.

(E) A mixture consisting of 6.38 g of celite, 7.25 g of Collins reagent ($Py_2.CrO_3$), and 1.95 g of 9α-hydroxy-16-methoxy-16-methyl-11α-,15-bis[(tetrahydro-1H-pyran-2-yl)]-prosta-13(E)-ene-1-oic acid methyl ester in 1890 ml of methylene chloride is stirred at room temperature for about 1 hour. The reaction mixture is poured into 1200 ml of ethyl ether and filtered througuh celite. The filtrate is decolorized with activated charcoal and concentrated to dryness. Yield: 1.77 g of 16-methoxy-16-methyl-9-oxo-11α,15-bis-[(tetrahydro-1H-pyran-2-yl)oxy]-prosta-13(E)-ene-1-oic acid methyl ester.

NMR spectrum in $CDCl_3$ (δ units): 0.93; 1.0–2.9; 1.12; 1.15; 3.1–4.9; 3.25; 3.32; 3.70; 5.4–5.8.

(F) The product thus obtained (1.77 g) is suspended in 100 ml of a solution of acetic acid:water:tetrahydrofuran 19:11:3 (v/v/v). After stirring at 45° C. for two hours, the mixture is diluted with water and the pH is brought to 7.2 by the addition of sodium bicarbonate.

The mixture is extracted with ethyl ether which is then boiled off yielding 1.19 g of a raw product which is purified by means of silica gel column chromatography by eluting with ethyl ether.

780 mg of pure 11α,15-dihydroxy-16-methoxy-16-methyl-9-oxo-prosta-13(E)-ene-1-oic acid methyl ester are obtained wherein the carbon atoms at positions 15 and 16 possess one of the four possible combinations of absolute configurations i.e. (15-R, 16-R) or (15-R, 16-S) or (15-S, 16-R) or (15-S, 16-S). The compound has the following characteristics:

NMR in $CDCl_3$ (δ): 0.92; 1.1–1.7; 1.11; 1.9–2.8; 2.29; 3.1–3.3; 3.24; 3.63; 4.07; 4.12; 5.69.

The compound is a unitary product, as evidentiated by differential scanning calorimetry, which melts at 40°–48° C.

(G) By starting from the less polar isomer of 9α-acetoxy-15-hydroxy-16-methoxy-16-methyl-11α-[(tetrahydro-1H-pyran-2-yl)oxy]-prosta-13(E)-ene-1-oic acid methyl ester, prepared as described under paragraph (C), and operating exactly as described under paragraphs (D), (E), and (F), 380 mg are obtained of 11α,15-dihydroxy-16-methoxy-16-methyl-9-oxo-prosta-13(E)-ene-1-oic acid methyl ester having at C-16 the same absolute configuration as the compound obtained under paragraph (F), but opposite absolute configuration at C-15. The compound has the following characteristics:

$[\alpha]_D^{20} = -79.6°$ (C=1% $CHCl_3$)

NMR spectrum in $CDCl_3$ (δ): 0.92; 1.1–1.7; 1.17; 1.9–2.8; 2.29; 3.26; 3.69; 4.10; 4.17; 5.75.

EXAMPLE 2

11α,15-dihydroxy-16-methoxy-16-methyl-9-oxo-prosta-13(E)-ene-1-oic acid methyl ester (15-R, 16-S) and (15-S, 16-S) or (15-R, 16-R) and (15-S, 16-R).

By operating substantially as described in example 1 but starting from the optical antipode of the phosphonate reagent employed under paragraph A of example 1, [$[\alpha]_D^{20} = -41.3°$ (C=1% in $CHCl_3$)] the other two possible isomers of 11α,15-dihydroxy-16-methoxy-16-methyl-9-oxo-prosta-13(E)-ene-1-oic acid methyl ester of formula I, are prepared. These two isomers have the same absolute configuration at C-16, which is opposite to the C-16 configuration of the two isomers of example 1, and opposite configurations at C-15.

(A) By condensing 5 g (0.0188 mole) of 3-methoxy-3-methyl-2-oxo-heptylphosphonic acid dimethyl ester having $[\alpha]_D^{20} = -41.3°$ (C=1% in $CHCl_3$) with 2.5 g (0.0080 mole) of 7-(5α-acetoxy-2β-formyl-3α-hydroxy-cyclopent-1α-yl)-heptanoic acid methyl ester as described under paragraph (A) of example 1 and then operating as described under paragraphs (B) and (C) of the same example, a mixture (2.65 g of raw product) of the two isomers at C-15 of 9α-acetoxy-15-hydroxy-16-methoxy-16-methyl-11α-[(tetrahydro-1H-pyran-2-yl)oxy]-prosta-13(E)-ene-1-oic acid methyl ester is obtained.

NMR spectrum in $CDCl_3$ (δ): 0.91; 1.0–2.6; 1.06; 1.07; 1.13; 1.14; 2.06; 2.29; 3.22; 3.24; 3.3–4.2; 3.68; 4.5–4.6; 5.13; 5.5–5.7.

(B) The mixture of two isomers at C-15 obtained above (2.65 g) is hydrolyzed by treatment with 78 ml of a solution acetic acid:water:tetrahydrofuran 19:11:3 (v/v/v) at 45° C. for 90 minutes. The reaction mixture is neutralized with sodium bicarbonate and extracted with ether. By evaporating the organic extract to dryness, 2.55 g of a raw product which is a mixture of the two C-15 isomers of 9α-acetoxy-11α,15-dihydroxy-16-methoxy-16-methyl-prosta-13(E)-ene-1-oic acid methyl ester is obtained. The pure isomers are separated by silica gel column chromatography by eluting with ethyl ether. The first eluted product is the less polar isomer (860 mg) having the following characteristics:

$[\alpha]_D^{20} = +17.3°$ (C=0.95% $CHCl_3$).

NMR spectrum in $CDCl_3$ (δ): 0.92; 1.05; 1.1–2.6; 2.07; 2.29; 3.23; 3.68; 3.93; 4.15; 5.19; 5.63.

The second eluted product is the more polar isomer (yield 870 mg) having the following characteristics:

$[\alpha]_D^{20} = +45.3°$ (C=0.76% in $CHCl_3$).

NMR spectrum in CDCl$_3$ (δ): 0.91; 1.0–1.7; 1.13; 2.07; 2.2–3.0; 2.29; 3.25; 3.68; 3.89; 4.15; 5.17; 5.53; 5.71.

(C) A mixture of 870 mg (0.00191 mole) of the more polar isomer prepared as described under paragraph (B), in 130 ml of anhydrous benzene, 30 mg of p-toluenesulfonic acid in 30 ml of anhydrous benzene and 2.5 ml (0.0273 mole) of 2,3-dihydropyran is kept at 15° C. for 15 minutes, then it is poured into an aqueous solution saturated with NaHCO$_3$ and the organic phase is separated. After washing with water, the organic phase is dried over Na$_2$SO$_4$ and evaporated to dryness.

The obtained residue is purified by chromatography using a silica gel column and eluting with petroleum ether:ethyl ether 7:3. Yield 1.09 g of 9α-acetoxy-16-methoxy-16-methyl-11α,15-bis-[(tetrahydro-1H-pyran-2yl)oxy]prosta-13(E)-ene-1-oic acid methyl ester having absolute configuration at C-16 opposite to that of the product prepared under paragraph (E) of example 1, and one of the two possible configurations at C-15.

NMR spectrum in CDCl$_3$ (δ): 0.92; 1.0–2.7; 1.11; 1.15; 2.05; 2.29; 3.22; 3.29; 3.3–4.2; 3.68; 4.6–4.9; 5.13; 5.4–5.8.

(D) By operating substantially as described under paragraphs (D) (last part), (F) and (G) of example 1, but starting from the compound obtained under paragraph (C) above, 250 mg of 11α,15-dihydroxy-16-methoxy-16-methyl-9-oxo-prosta-13(E)-ene-1-oic acid methyl ester are obtained.

This product has the following characteristics:

$[\alpha]_D^{20} = -51.4°$ (C=0.52% in CHCl$_3$)

NMR spectrum in CDCl$_3$ (δ):: 0.91; 1.1–3.2; 1.14; 2.30; 3.25; 3.68; 4.07; 4.10; 5.6–6.0.

(E) By operating as described in paragraphs (C) and (D) of this example, but starting from the less polar isomer obtained in paragraph (B) (860 mg), 320 mg of 11α,15-dihydroxy-16-methoxy-16-methyl-9-oxo-prosta-13(E)-ene-1-oic acid methyl ester are obtained. Said compound which has the same absolute configuration at C-16 as the corresponding isomer prepared under paragraph (D) and opposite configuration at C-15, shows the following characteristics:

$[\alpha]_D^{20} = -82.4°$ (C=0.95% in CHCl$_3$)

NMR spectrum in CDCl$_3$ (δ): 0.94; 1.1–1.8; 1.06; 2.0–2.9; 2.30; 3.24; 3.69; 4.11; 4.19; 5.6–5.9;

EXAMPLE 3

A capsule is prepared containing the following ingredients:

| | |
|---|---|
| 11α,15-dihydroxy-16-methoxy-16-methyl-9-oxo-prosta-13(E)-ene-1-oic acid methyl ester | 40 μg |
| Talc | 3 mg |
| Lactose | 3 mg |
| Sodium-carboxymethylcellulose | 3 mg |
| Starch | q.s. to 90 mg |

EXAMPLE 4

A coated tablet is prepared with:

| | |
|---|---|
| 11α,15-dihydroxy-16-methoxy-16-methyl-9-oxo-prosta-13(E)-ene-1-oic acid methyl ester | 60 μg |
| Sodium-carboxymethylcellulose | 4 mg |
| Magnesium stearate | 4 mg |
| Gelatin | 7 mg |
| Starch | 7 mg |
| Saccarose | 20 mg |
| arabic gum, lactose, titanium dioxide, aluminum lac according to conventional methods. | |

I claim:

1. 15R,16R,-16-methoxy-16-methyl prostaglandin E$_1$ derivatives of the general formula wherein R stands for a (C$_{1-4}$)alkyl group or a non-toxic, pharmaceutically acceptable cation.

2. The stereoisomer of the 11α-15-dihydroxy-16-methoxy-16-methyl-9-oxo-prosta-13-(E)-ene-1-oic acid methyl ester having a chirality at C$_{16}$ corresponding to that at C$_3$ of the stereoisomer of 3-methoxy-3-methyl-2-oxo-hepthyl-phosphonic acid dimethyl ester which as an $[\alpha]_D^{20}$ of +41.2°, (c=1%, CHCl$_3$), and having a chirality at C$_{15}$ corresponding to that of the more polar stereoisomer of 9-acetoxy-15-hydroxy-16-methoxy-16-methyl-11α-[(tetrahydro-1H-pyran-2-yl)oxy]prosta-13(E)-ene-1-oic acid methyl ester, which is the second eluted product in a chromatographic separation of stereoisomers on silica gel using sequentially a mixture petroleum ether/ethyl ether 8:2, (v/v), and then petroleum ether/ethyl ether 6:4, (v/v).

3. A pharmaceutical composition useful for protecting the gastric mucosa in mammals which contain from 5 to 100 μg of a compound of claim 1 as the active ingredient, in admixture with a pharmaceutically acceptable carrier.

4. A method of protecting the gastric mucosa from ulceration in patients in need thereof which comprises administering to said patients an effective gastric mucosa protecting amount of a compound of claim 1.

5. A method according to claim 4 wherein the effective amount comprises a daily dosage of from 10 to 300 μg.

* * * * *